(12) United States Patent
Allan et al.

(10) Patent No.: US 8,666,705 B2
(45) Date of Patent: Mar. 4, 2014

(54) METHODS AND APPARATUS FOR PREDICTING GLASS PROPERTIES

(75) Inventors: Douglas Clippinger Allan, Corning, NY (US); Adam James Ellison, Painted Post, NY (US); John Christopher Mauro, Corning, NY (US)

(73) Assignee: Corning Incorporated, Corning, NY (US)

( * ) Notice: Subject to any disclaimer, the term of this patent is extended or adjusted under 35 U.S.C. 154(b) by 489 days.

(21) Appl. No.: 12/896,355

(22) Filed: Oct. 1, 2010

(65) Prior Publication Data

US 2012/0083915 A1    Apr. 5, 2012

(51) Int. Cl.
| | |
|---|---|
| *G06F 7/60* | (2006.01) |
| *G06F 17/10* | (2006.01) |
| *G06G 7/48* | (2006.01) |
| *G06G 7/58* | (2006.01) |
| *C03B 5/24* | (2006.01) |
| *C03B 9/41* | (2006.01) |

(52) U.S. Cl.
USPC .................. 703/2; 703/12; 65/29.1; 65/29.11

(58) Field of Classification Search
USPC ...................... 703/2, 12; 65/17.1, 29.1, 29.11
See application file for complete search history.

(56) References Cited

U.S. PATENT DOCUMENTS 6,687,621 B2    2/2004    Schneiderman et al.

OTHER PUBLICATIONS

Hrma, P. "Glass viscosity as a function of temperature and composition: A model based on Adam-Gibbs equation." Journal of Non-Crystalline Solids 354.29 (2008): 3389-3399.*

Rekhson, S. M., and G. W. Scherer. "Glass Transition as a Function of Cooling Rate." Le Journal de Physique Colloques 43.C9 (1982): C9-427.*

Fluegel, Alexander. "Glass viscosity calculation based on a global statistical modelling approach." Glass Technology—European Journal of Glass Science and Technology Part A 48.1 (2007): 13-30.*

Azzou, Adila, et al. "Experiments and Model Simulations of the Viscosity and Dilatation of Glass Coatings with Temperature Dependence." Journal of the American Ceramic Society 92.3 (2009): 616-622.*

Sturm VKG (1980) Zur Temperaturabhängigkeit der viskosität von flüssigkeiten. *Glastechn Ber* 53:63-76.

Adam et al, "On the Temperature Dependence of Cooperative Relaxation Properties in Glass-Forming Liquids," 1965, J. Chem. Phys. 43:139-146.

Angell CA (1995) Formation of Glasses from Liquids and Biopolymers, Science 267:1924-1935.

Avramov, L., Milchev, A., "Effect of Disorder on Diffusion and Viscosity in Condensed Systems," 1988, J. Non-Crystalline Solids, 104:253-260.

Dyre et al, "Fundamental Questions Relating to Ion Conduction in Disordered Solids," Rep. Prog. Phys., 72, 046501 (2009).

(Continued)

*Primary Examiner* — Aniss Chad
(74) *Attorney, Agent, or Firm* — Robert L. Carlson

(57) ABSTRACT

Methods and apparatus for predicting viscosities of glass materials as a function of temperature and composition are provided. Two fitting parameters (fitting coefficients) are used for each of the viscosity-affecting components contained in the material. The parameters can accurately cover a wide range of temperatures (i.e., a wide range of viscosities) and a wide range of compositions. The viscosity predictions can be used as a guide for glass research as well as in feedback control systems for glass manufacturing processes. Methods and apparatus for predicting glass resistivity are also disclosed.

31 Claims, 7 Drawing Sheets

(56) References Cited

OTHER PUBLICATIONS

Fuegel et al, "Electrical Resistivity of Silicate Glass Melts Calculation Based on the SciGlass Database," 2007 available online at http://glassproperties.com.
Gupta et al, "Composition Dependence of Glass Transition Temperature and Fragility," I. A topological modal incorporating temperature-dependent constraints, J. Chem. Phys. 130:094503.
Hrma, Pavel, Arrhenius Model for High-Temperature Glass Viscosity Exponential Factor, Journal of Non-Crystalline, vol. 354, Issue 18, Apr. 15, 2008.
Hrma, Pavel, "Glass Viscosity as a Function of Temperature and Composition: A Model Based on Adam-Gibbs Equation," Journal of Non-Crystalline, vol. 354, Issue 29, Jul. 1, 2008.
Hrma, Pavel, "Viscosity of Many-Component Glasses," Journal of Non-Crystalline, vol. 355, Issues 14-15, Jun. 1, 2009.
Hutton at al, Amorphous Materials, eds Douglas RW, Ellis B (John Wiley & Sons, New York, 1972), p. 215.
Laughlin, "Viscous Flow in Simple Organic Liquids," The Journal of Physical Chemistry, vol. 76, No. 16, 1972.
Mauro, "Viscosity of Glass-Forming Liquids," PNAS, 19780-19784, Nov. 24, 2009; vol. 106, No. 47.
Mazurin et al, "Electrical Conductivity of Glass Melts," Properties of Glass-Forming Melts, ed. By L.D. Pye, A Montenem, and I, Joseph, pp. 295-333 (CRC Press, Taylor & Francis Group, Boca Raton, FL 2005.
Naumis Gerardo, "Glass Transition Phenomenology and Flexibility Energy Landscape Formalism," Journal of Non-Crystalline vol. 352, issues 42-49, Nov. 15, 2006.
Phillips, J.C., "Topology of Covalent Non-Crystalline SolidsI; Short-Range Order in Chaleogenide Alloys," Journal of Non-Crystalline, vol. 34, Issue 2, Oct.-Nov. 1979.
Phillips, J.C., "Constraint Theory, Vector Percolation, and Glass Formation", Solid State Communication, vol. 53, Issue 8, Feb. 1985.
Scherer, George W., "Editorial Comments on a Paper by Gordon S. Fulcher", Journal Am. Ceram. Soc., 75(5), 1060-62, 1992.
Sturm VKG 1980 Zur Temperaturabhagnigkeit der viskositat von flussigkeiten, Glastechn Ber53:63-76.
Utracki LA 1974 "Temperature Dependence of Liquid Viscosity,"J. Macromol Sci B, 10:477-505.
Varshneya, Arun, "Fundamentals of Inorganic Glasses,"SGT News, No. 6, 2005.
Waterton, SC, The Viscosity-Temperature Relationship and Some Inferences on the Nature of Molten and of Plastic Glass, J. Soc. Glass Technol., 16:244-249.
Williams, Malcolm L., "The Temperature Dependence of Relaxation Mechanisms in Amorphous Polymers and Other Glass-Forming Liquids," Jul. 20, 1955.
Wondraczek, Lothar, "Advancing Glasses Through Fundamental Research," Journal of the European Ceramic Society, vol. 29, Issue 7, Apr. 2009.

* cited by examiner

METHODS AND APPARATUS FOR PREDICTING GLASS PROPERTIES

FIELD

This disclosure relates to methods and apparatus for predicting the equilibrium viscosity and/or electrical resistivity of glasses and/or glass-forming liquids (hereinafter referred to as "glass materials" or simply "materials").

More particularly, it relates to measuring the viscosities and/or resistivities of a plurality of glass materials at a plurality of temperatures, using the measured viscosities and/or resistivities and a programmed computer to obtain empirical fitting constants, and then using the empirical fitting constants and a programmed computer to predict viscosities and/or resistivities for the same and/or different glass materials at the same and/or different temperatures.

DEFINITIONS AND CONVENTIONS

Bold letters are used herein to indicate parameters and/or variables which comprise a set of values and thus may be thought of as a vector, i.e., x is used to represent a composition vector, and FC1, FC2, FC$^p$1, and FC$^p$2 are used to represent fitting coefficient vectors.

The terms "viscosity," "shear viscosity," and "equilibrium viscosity" are used interchangeably herein to refer to equilibrium shear viscosity.

The terms "resistivity" and "electrical resistivity" are used interchangeably herein to refer to electrical resistivity.

All viscosities referred to herein are assumed to have been divided by their units, e.g., Pa-s, to make numbers upon which the log function can operate. Similarly, all electrical resistivities are assumed to have been divided by their units, e.g., ohm-meters.

As used herein, the glass transition temperature of a material is the temperature at which it has a viscosity of $10^{12}$ Pa-s.

BACKGROUND

The problem of predicting the properties of glass materials has been a longstanding one in the field of glass and glass-ceramic chemistry. Because most glasses and glass-ceramics (hereinafter referred to collectively as "glasses") contain a relatively large number of components, e.g., three to a half-a-dozen or more in many cases, the compositional space is multi-dimensional, making experimental study of the entire space economically impractical. Yet, from melting through to forming, the production of glass articles would clearly benefit from an ability to predict glass properties based on glass composition or, conversely, to select glass compositions based on desired properties.

Among all the technologically useful properties of a glass-forming system, the shear viscosity $\eta$ of the melt is undoubtedly the most important. Every stage of industrial glass production—from the initial melting, mixing, and fining to the final forming operations—requires careful control of shear viscosity. For example, shear viscosity controls the rates of melting and of fining in a glass melting tank. Similarly, each glass forming operation, e.g., fiber forming or the final annealing of container glass, requires a certain well-defined viscosity range and consequently a specific temperature range for that operation. See, for example, Varshneya A K (2006) *Fundamentals of Inorganic Glasses,* 2nd ed. (Society of Glass Technology, Sheffield, UK). Viscosity also determines the relaxation rate of a final glass product. For example, viscosity controls the compaction behavior of display glasses (e.g., the glass sheets used as substrates in the production of liquid crystal displays) during customer heat treatment cycles. It should thus come as no surprise that the details of the viscosity-temperature relationship play a critical role in researching new glass compositions for display and other applications.

Among other reasons, the problem of relating viscosity to temperature and composition is challenging because from the initial glass melting to final forming, viscosity varies by over twelve orders of magnitude. See, for example, Varshneya (2006), supra. Viscosity is also sensitive to small changes in composition, especially in silicate melts where small levels of impurities can have a profound influence on the flow behavior. It is thus of great importance to have accurate knowledge of the scaling of viscosity with both composition (x) and temperature (T). Unfortunately, measurement of $\eta(T,x)$ is challenging for high temperature melts, and low temperature measurements (i.e., in the high viscosity range, $10^{10}$ to $10^{15}$ Pa-s) are time consuming and often prohibitively expensive. See, for example, Varshneya (2006), supra. It is therefore of great interest to develop an accurate model of $\eta(T,x)$.

Resistive furnaces require melts within a range of electrical resistivity values to ensure proper glass melting behavior and to avoid destruction of the tank refractory. The electrical resistivity of disordered media has drawn much interest from physicists due to the strong frequency dependence of the measured conductivity. See, for example, J. C. Dyre, P. Maass, B. Roling, and D. L. Sidebottom, "Fundamental Questions Relating to Ion Conduction in Disordered Solids," *Rep. Frog. Phys.,* 72, 046501 (2009). This frequency dependence is a direct result of inhomogeneities leading to a distribution of activation barriers for electrical conduction. While the universal frequency dependence of ac conductivity has received much attention, there has been little work addressing the temperature and composition dependences of conductivity at a fixed frequency. Most models assume an Arrhenius dependence of resistivity with temperature, despite the fact that as recognized as part of this disclosure, the same inhomogeneities that lead to a frequency-dependent conductivity must also lead to a non-Arrhenius dependence on temperature. As to the composition dependence of resistivity, the work that exists is based on strictly empirical fits, e.g., on Taylor series expansions of the coefficients of the Vogel-Fulcher-Tammann (VFT) relation. See, for example, O. V. Mazurin and O. A. Prokhorenko, "Electrical Conductivity of Glass Melts," in *Properties of Glass-Forming Melts,* ed. by L. D. Pye, A. Montenero, and I. Joseph, pp. 295-338 (CRC Press, Taylor & Francis Group, Boca Raton, Fla., 2005); and A. Fluegel, D. A. Earl, and A. K. Varshneya, "Electrical Resistivity of Silicate Glass Melts Calculation Based on the SciGlass Database," available online at http://glassproperties.com (2007).

Pavel Hrma of the Pacific Northwest National Laboratory (Richland, Wash.) reports an empirical model for the dependence of equilibrium viscosity as a function of temperature and composition. See P. Hrma, "Glass viscosity as a function of temperature and composition: A model based on Adam-Gibbs equation," *J. Non-Cryst. Solids,* 354, 3389-3399 (2008). Hrma's model is based on the Adam-Gibbs equation, with the assumption in Hrma's Eq. (4) of a power law dependence for the configurational entropy. This assumption can lead to zero entropy (i.e., infinite viscosity) at a finite temperature, a physically dubious result. From a practical point of view, this means that viscosity predictions based on Hrma's model will suffer at low temperatures (i.e., high viscosities).

As to the composition dependence of viscosity, in Eqs. (8) and (9), Hrma includes composition dependence via linear expansions of the glass transition temperature and his $s_0$ parameter in terms of the oxide components of the glass. However, as recognized as part of this disclosure, glass transition temperature cannot be expanded in such a manner over a wide range of compositions. For example, in borosilicate glasses the addition of sodium first causes a conversion of boron from three to four coordination, increasing the glass transition temperature. Then additional sodium creates non-bridging oxygens which subsequently decrease the glass transition temperature. Other examples include alkali or alkaline earth addition to aluminosilicate glasses and mixed alkali silicate glasses. Consequently, Hrma's linear expansion of the glass transition temperature is valid over only a narrow range of compositions. Hrma's second expansion is a linear expansion of his $s_0$ parameter with respect to the oxide composition. As recognized as part of this disclosure, Hrma's expansion of $s_0$ is analogous to an expansion of the $T_0$ parameter in the VFT expansion. This is also unphysical. The result of this expansion is an overprediction of low temperature viscosities and an overprediction of fragility.

In view of this state of the art, a need exists for more effective methods and apparatus for predicting the properties of glass materials and, in particular, for predicting the dependence of viscosity and/or resistivity on temperature and/or composition. The present disclosure addresses these problems.

SUMMARY

In accordance with a first aspect, for a material that (a) is a glass or glass-forming liquid and (b) includes N viscosity-affecting components, a method is disclosed that includes:

(A) using a computer to evaluate an equation which relates equilibrium viscosity $\eta$ and temperature T and has the following form:

$$\log_{10}\eta(T,x)=C_1+C_2\cdot(f_1(x,FC1)/T)\cdot\exp([f_2(x,FC2)-1]\cdot[f_1(x,FC1)/T-1])$$

where
(i) $C_1$ and $C_2$ are constants,
(ii) $x=\{x_1, x_2, \ldots x_i \ldots x_N\}$ are the concentrations of the N viscosity-affecting components,
(iii) $FC1=\{FC^1_1, FC^1_2 \ldots FC^1_i \ldots FC^1_N\}$ is a first set of empirical, temperature-independent fitting coefficients, one coefficient for each of the N viscosity-affecting components, and
(iv) $FC2=\{FC^2_1, FC^2_2 \ldots FC^2_i \ldots FC^2_N\}$ is a second set of empirical, temperature-independent fitting coefficients, one coefficient for each of the N viscosity-affecting components; and (B) using the results of step (A) to provide at least one of: (i) a predicted equilibrium viscosity $\eta$ of the material at a temperature T, and (ii) a predicted temperature T at which the material has an equilibrium viscosity $\eta$.

In accordance with a second aspect, a method is disclosed for identifying at least one material expected to have at least one desired $\eta$,T pair, where $\eta$ is equilibrium viscosity and T is temperature, the method including:

(A) selecting at least one candidate material which includes N viscosity-affecting components having selected concentrations, where N may be different for different candidate materials;

(B) using a computer to obtain at least one $\eta$,T pair for the at least one candidate material of step (A) by evaluating an expression of the form $$\log_{10}\eta(T,x)=C_1+C_2\cdot(f_1(x,FC1)/T)\cdot\exp([f_2(x,FC2)-1]\cdot[f_1(x,FC1)/T-1])$$

where
(i) $C_1$ and $C_2$ are constants,
(ii) $x=\{x_1, x_2, \ldots x_i \ldots x_N\}$ are the concentrations of the N viscosity-affecting components,
(iii) $FC1=\{FC^1_1, FC^1_2 \ldots FC^1_i \ldots FC^1_N\}$ is a first set of empirical, temperature-independent fitting coefficients, one coefficient for each of the N viscosity-affecting components, and
(iv) $FC2=\{FC^2_1, FC^2_2 \ldots FC^2_i \ldots FC^2_N\}$ is a second set of empirical, temperature-independent fitting coefficients, one coefficient for each of the N viscosity-affecting components;

(C) comparing the at least one $\eta$,T pair resulting from step (B) with the at least one desired $\eta$,T pair; and (D) repeating steps (A) to (C) as necessary until at least one candidate material is selected in step (A) which gives at least one $\eta$,T pair in step (B) which satisfies at least one selected criterion relative to the at least one desired $\eta$,T pair, said at least one candidate material being the at least one material expected to have the at least one desired $\eta$,T pair.

In accordance with a third aspect, a method is disclosed for determining a relationship between temperature T and viscosity $\eta$ for a material that (i) is a glass or glass-forming liquid and (ii) includes N viscosity-affecting components, the method including:

(a) measuring the viscosity of a plurality of reference materials at a plurality of temperatures; and (b) using a programmed computer, fitting a function of the form $$\log_{10}\eta(T,x)=C_1+C_2\cdot(f_1(x,FC1)/T)\cdot\exp([f_2(x,FC2)-1]\cdot[f_1(x,FC1)/T-1])$$

to the measured viscosities of step (a) to determine values for FC1 and FC2, where in said function:
(i) $C_1$ and $C_2$ are constants,
(ii) $x=\{x_1, x_2, \ldots x_i \ldots x_N\}$ are the concentrations of the N viscosity-affecting components,
(iii) $FC1=\{FC^1_1, FC^1_2 \ldots FC^1_i \ldots FC^1_N\}$ is a first set of temperature-independent coefficients, one coefficient for each of the N viscosity-affecting components, and
(iv) $FC2=\{FC^2_1, FC^2_2 \ldots FC^2_i \ldots FC^2_N\}$ is a second set of temperature-independent coefficients, one coefficient for each of the N viscosity-affecting components,
the function and the values for FC1 and FC2 determined in step (b) constituting the relationship between viscosity and temperature for the material.

In accordance with a fourth aspect, for a material that (a) is a glass or glass-forming liquid and (b) includes N' resistivity-affecting components, a method is disclosed that includes:

(A) using a computer to evaluate an equation which relates resistivity $\rho$ and temperature T and has the following form:

$$\log_{10}\rho(T,x)=C^\rho_1+C^\rho_2\cdot(f_1(x,FC^\rho 1)/T)\cdot\exp([f_2(x,FC^\rho 2)-1]\cdot[f_1(x,FC^\rho 1)/T-1])$$

where
(i) $C^\rho_1$ and $C^\rho_2$ are constants,
(ii) $x=\{x_1, x_2, \ldots x_i \ldots x_{N'}\}$ are the concentrations of the N' resistivity-affecting components,
(iii) $FC^\rho 1=\{FC^\rho_1, FC^\rho_2 \ldots FC^\rho_i \ldots FC^\rho_{N'}\}$ is a first set of empirical, temperature-independent fitting coefficients, one coefficient for each of the N' resistivity-affecting components, and (iv) $FC^p2=\{FC^p_1, FC^p_2 \ldots FC^p_i \ldots FC^p_{N'}\}$ is a second set of empirical, temperature-independent fitting coefficients, one coefficient for each of the N' resistivity-affecting components, and (B) using the results of step (A) to provide at least one of: (i) a predicted resistivity ρ of the material at a temperature T, and (ii) a predicted temperature T at which the material has a resistivity ρ.

In accordance with a fifth aspect, a method is disclosed for identifying at least one material expected to have at least one desired ρ,T pair, where ρ is resistivity and T is temperature, the method including:

(A) selecting at least one candidate material which includes N' resistivity-affecting components having selected concentrations, where N' may be different for different candidate materials;

(B) using a computer to obtain at least one ρ,T pair for the at least one candidate material of step (A) by evaluating an expression of the form $$\log_{10}\rho(T,x)=C^p_1+C^p_2\cdot(f_1(x,FC^p1)/T)\cdot\exp([f_2(x,FC^p2)-1]\cdot[f_1(x,FC^p1)/T-1])$$

where
(i) $C^p_1$ and $C^p_2$ are constants,
(ii) $x=\{x_1, x_2, \ldots x_i \ldots x_{N'}\}$ are the concentrations of the N' resistivity-affecting components,
(iii) $FC^p1=\{FC^p_1, FC^p_2 \ldots FC^p_i \ldots FC^p_{N'}\}$ is a first set of empirical, temperature-independent fitting coefficients, one coefficient for each of the N' resistivity-affecting components, and
(iv) $FC^p2=\{FC^p_1, FC^p_2 \ldots FC^p_i \ldots FC^p_{N'}\}$ is a second set of empirical, temperature-independent fitting coefficients, one coefficient for each of the N' resistivity-affecting components, (C) comparing the at least one ρ,T pair resulting from step (B) with the at least one desired ρ,T pair; and (D) repeating steps (A) to (C) as necessary until at least one candidate material is selected in step (A) which gives at least one ρ,T pair in step (B) which satisfies at least one selected criterion relative to the at least one desired ρ,T pair, said at least one candidate material being the at least one material expected to have the at least one desired ρ,T pair.

In accordance with a sixth aspect, a method is disclosed for determining a relationship between temperature T and resistivity ρ for a material that (i) is a glass or glass-forming liquid and (ii) includes N' resistivity-affecting components, the method including:

(a) measuring the resistivity of a plurality of reference materials at a plurality of temperatures; and (b) using a programmed computer, fitting a function of the form $$\log_{10}\rho(T,x)=C^p_1+C^p_2\cdot(f_1(x,FC^p1)/T)\cdot\exp([f_2(x,FC^p2)-1]\cdot[f_1(x,FC^p1)/T-1])$$

to the measured resistivities of step (a) to determine values for $FC^p1$ and $FC^p2$, where in said function:
(i) $C^p_1$ and $C^p_2$ are constants,
(ii) $x=\{x_1, x_2, \ldots x_i \ldots x_{N'}\}$ are the concentrations of the N' resistivity-affecting components,
(iii) $FC^p1=\{FC^p_1, FC^p_2 \ldots FC^p_i \ldots FC^p_{N'}\}$ is a first set of temperature-independent coefficients, one coefficient for each of the N' resistivity-affecting components, and
(iv) $FC^p2=\{FC^p_1, FC^p_2 \ldots FC^p_i \ldots FC^p_{N'}\}$ is a second set of temperature-independent coefficients, one coefficient for each of the N' resistivity-affecting components, the function and the values for $FC^p1$ and $FC^p2$ determined in step (b) constituting the relationship between resistivity and temperature for the material.

Apparatus for practicing the above methods, specifically, programmed computers and computer readable storage media, is also disclosed.

The above summaries of the various aspects of the disclosure are only for the convenience of the reader and are not intended to and should not be interpreted as limiting the scope of the invention. More generally, it is to be understood that both the foregoing general description and the following detailed description are merely exemplary of the invention and are intended to provide an overview or framework for understanding the nature and character of the invention.

Additional features and advantages of the invention are set forth in the detailed description which follows, and in part will be readily apparent to those skilled in the art from that description or recognized by practicing the invention as exemplified by the description herein. The accompanying drawings are included to provide a further understanding of the invention, and are incorporated in and constitute a part of this specification.

It is to be understood that the various features of the invention disclosed in this specification and in the drawings can be used in any and all combinations. In this regard, it should be noted that dependent claims have only been explicitly set forth with regard to some of the independent claims, it being understood that the similar dependent claims are applicable to the remaining independent claims, including the resistivity claims where the requisite adjustments to the claim language will be evident to the skilled reader from the present disclosure. For example, when dependent on independent Claim 31, dependent Claim 10 will refer to resistivity-affecting components rather than viscosity-affecting components. Likewise, when dependent on independent Claim 30, dependent Claim 25 will refer to ρ being less than a first selected value rather than η. Similar language/symbol changes will be readily recognized by a skilled person with regard to the remainder of the independent and dependent claims.

DETAILED DESCRIPTION

Figure 1:
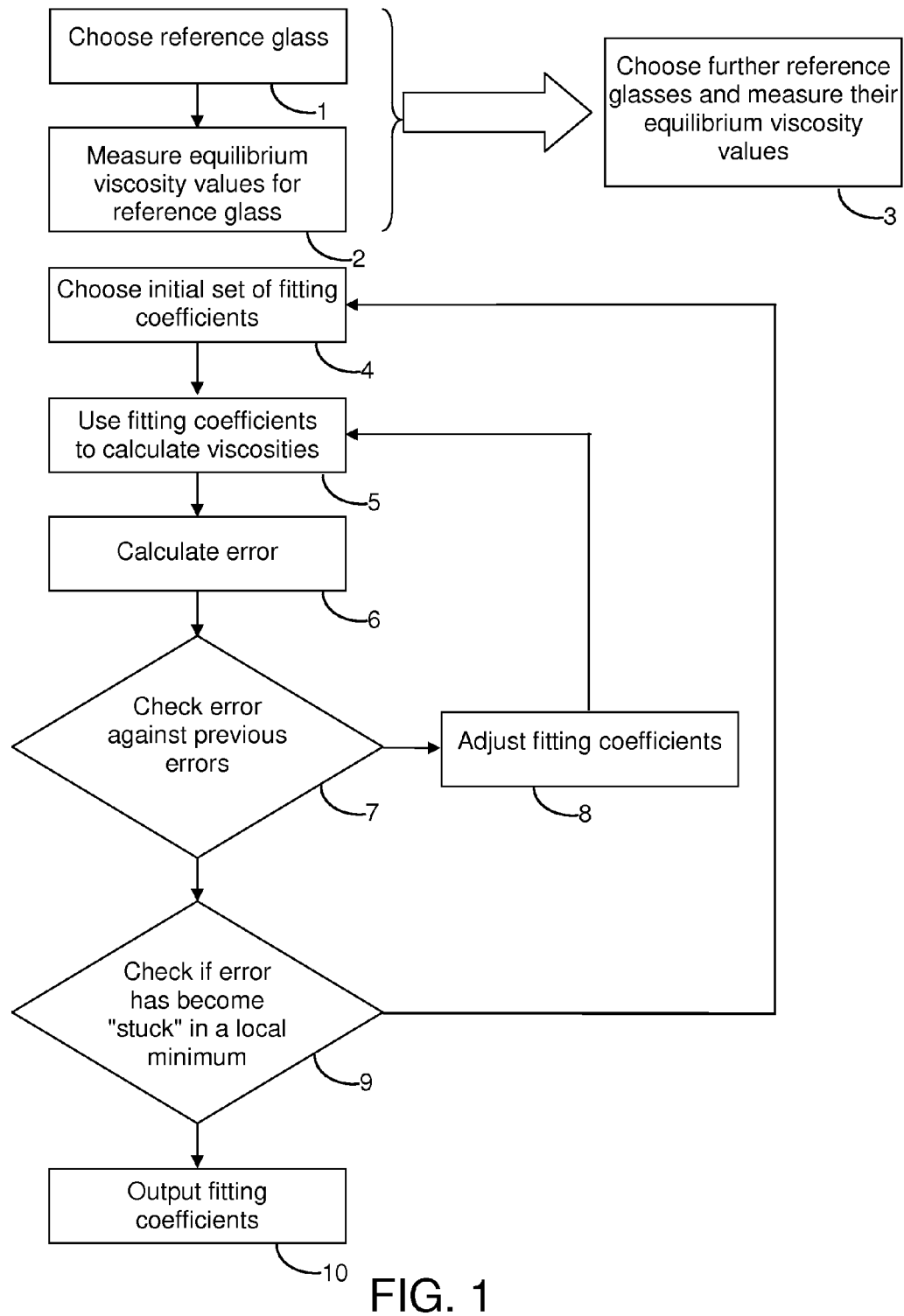
FIG. 1 is a flowchart showing a representative sequence of steps that can be used with a programmed computer to determine fitting coefficients for embodiments of the present disclosure.

As indicated above, the methods and apparatus for predicting viscosity disclosed herein have as their base an equation of the form:

$$\log_{10}\eta(T,x) = C_1 + C_2 \cdot (f_1(x,FC1)/T) \cdot \exp([f_2(x,FC2)\Box 1] \cdot [f_1(x,FC1)/T-1]), \quad \text{Eq. (1)}$$

where $C_1$, $C_2$, x, FC1, and FC2 are as defined above in the Summary. With regard to the viscosity-affecting components included in the vector x, it should be noted that those components can include clusters of constituents and/or constituents that might in some contexts be considered contaminants, e.g., water which would be considered a contaminant in, for example, glasses used in optical waveguide fibers. In many cases, the basic constituents of the glass will be oxides, it being understood that Eq. (1) can also be used with non-oxide glasses if desired. As to units, the composition can be expressed in any convenient units desired by the user, mole percent and weight percent being the most common choices.

Although equations of various forms have been proposed to relate viscosity to temperature and composition, the above form has been found to provide better predictions over a wider range of compositions and temperatures than those proposed in the past. For example, in the Hrma paper discussed above, Hrma applies his composition-dependent model to viscosities less than $10^{2.5}$ Pa-s only (see Hrma's FIG. 4), whereas Eq. (1) has been successfully applied to viscosities as high as $10^{11}$ Pa-s, over eight orders of magnitude higher. Also, as shown in Hrma's FIG. 5, Hrma's approach results in a large scatter between calculated and measured values of glass transition temperature, while predictions based on Eq. (1) are much more accurate over a much wider range of compositions. Furthermore, as shown in Hrma's FIG. 6, when Hrma attempts to use his model for high viscosities, the error becomes much larger, even for a small set of compositions, a problem that does not occur when an equation of the form of Eq. (1) is used. In addition, Hrma uses completely different parameters values for different sets of glasses (i.e., float glasses vs. waste glasses), while when an equation of the form of Eq. (1) is used, a common set of parameters can be employed for a wide range of glasses.

In an embodiment, Eq. (1) can be of the specific form:

$$\log_{10}\eta(T, x) = \log_{10}\eta_\infty + (12 - \log_{10}\eta_\infty)\frac{T_g(x)}{T}\exp\left[\left(\frac{m(x)}{12 - \log_{10}\eta_\infty} - 1\right)\left(\frac{T_g(x)}{T} - 1\right)\right], \quad \text{Eq. (2)}$$

where $\eta_\infty$ is the extrapolated infinite temperature viscosity (a universal constant which is independent of composition and temperature), $T_g(x)$ is the composition-dependent glass transition temperature, and m(x) is the composition-dependent fragility, which is defined as:

$$m(x) = \frac{\partial \log_{10}\eta(T, x)}{\partial(T_g(x)/T)}\bigg|_{T=T_g(x)}. \quad \text{Eq. (3)}$$

Comparing Eq. (2) to Eq. (1), we see that in this embodiment:

$C_1 = \log_{10}\eta_\infty$, and $C_2 = 12 - \log_{10}\eta_\infty$ (or, equivalently, $C_2 = 12 - C_1$).

As to FC1 and FC2, these are based on expansions of the glass transition temperature $T_g(x)$ and fragility m(x), respectively. Beginning with the glass transition temperature expansion, this expansion can be derived from constraint theory, which makes the expansion inherently nonlinear in nature. The fragility expansion can be written in terms of a superposition of contributions to heat capacity curves, a physically realistic scenario. The net result of the choice of these expansions is that Eq. (1) can accurately cover a wide range of temperatures (i.e., a wide range of viscosities) and a wide range of compositions.

As a specific example of a constraint theory expansion of glass transition temperature, the composition dependence of $T_g$ can, for example, be given by an equation of the form:

$$f_1(x, FC1) = T_g(x) = \frac{K_R}{d - \sum_i x_i n_i / \sum_j x_j N_j}, \quad \text{Eq. (4)}$$

where the $n_i$'s are the $FC^1_i$'s, d is the dimensionality of space (normally, d=3), the $N_j$'s are the numbers of atoms in the viscosity-affecting components (e.g., N=3 for $SiO_2$, N=5 for $Al_2O_3$, and N=2 for CaO), and $K_R$ is a scaling parameter for a selected reference material R, the scaling parameter being given by:

$$K_R = T_g(x_R)\left(d - \frac{\sum_i x_{R,i} n_i}{\sum_j x_{R,j} N_j}\right), \quad \text{Eq. (5)}$$

where $T_g(x_R)$ is a glass transition temperature for the reference material obtained from at least one viscosity measurement for that material.

The summations in Eqs. (4) and (5) are over each viscosity-affecting component i and j of the material, the $x_i$'s can, for example, be expressed as mole fractions, and the $n_i$'s can, for example, be interpreted as the number of rigid constraints contributed by the various viscosity-affecting components. In Eqs. (4) and (5), the specific values of the $n_i$'s are left as empirical fitting parameters (fitting coefficients). Hence, in the calculation of $T_g(x)$ there is one fitting parameter for each viscosity-affecting component i.

As a specific example of a fragility expansion based on a superposition of heat capacity curves, the composition dependence of m can, for example, be given by an equation of the form:

$$f_2(x, FC2) = m(x)/m_0 = \left(1 + \sum_i x_i \frac{\Delta C_{p,i}}{\Delta S_i}\right), \quad \text{Eq. (6)}$$

where the $$\frac{\Delta C_{p,i}}{\Delta S_i}\text{'s}$$

are the $FC2_i$'s, $m_0$ is $C_2$, (i.e., $m_0=12-\log_{10}\eta_\infty$), the $\Delta C_{p,i}$'s are changes in heat capacity at the glass transition, and the $\Delta S_i$'s are entropy losses due to ergodic breakdown at the glass transition. The constant $m_0$ can be interpreted as the fragility of a strong liquid (a universal constant). Although workers in the art have previously believed that $m_0$ is in the range of 16-17, in accordance with the present work, it has been found that $m_0$ is less than 16 and greater than or equal to 14, e.g., $m_0$ is approximately equal to 14.9.

The values of $\Delta C_{p,i}/\Delta S_i$ in Eq. (6) are left as empirical fitting parameters (fitting coefficients) for each viscosity-affecting component i. Hence, the complete viscosity model involves only two fitting parameters per viscosity-affecting component, i.e., $n_i$ and $\Delta C_{p,i}/\Delta S_i$, where the $n_i$'s are the $FC^1_i$'s and the $\Delta C_{p,i}/\Delta S_i$'s is are the $FC^2_i$'s of Eq. (1).

Although the use of glass transition temperature and fragility are preferred approaches for developing expressions for $f_1(x,FC1)$ and $f_2(x,FC2)$ in Eq. (1), other approaches can be used, if desired. For example, the strain point or the softening point of the glass, together with the slope of the viscosity curves at these temperatures can be used.

Once specific $f_1(x,FC1)$ and $f_2(x,FC2)$ expressions have been selected, values for the $FC1_i$'s and the $FC2_i$'s need to be determined FIG. 1 sets forth in a flowchart format a suitable computer-based procedure that can be used for this purpose, it being understood that this flowchart is for illustration purposes only and that a variety of other computer-based approaches for determining the $FC^1_i$'s and $FC^2_i$'s values will be evident to skilled persons from the present disclosure and can be used if desired.

Steps 1-3 of FIG. 1 relate to the experimental portion of the process. Thus, in step 1, a reference glass composition j is chosen which is given by $\{x_i\}_j$ for i from 1 to $N_j$ for $N_j$ viscosity-affecting components, and in step 2, equilibrium viscosity values are measured at $M_j$ temperature points for the glass of step 1. Reference number 3 represents repeating steps 1 and 2 for P distinct reference glass compositions and collecting all the results into a table that relates viscosities and temperatures with compositions. Typically, the P distinct reference glass compositions will be chosen so as to span the compositional space of interest. However, this need not necessarily be the case since expressions for $\eta(T,x)$ having the form of Eq. (1) are capable of extrapolation outside of the compositional space defined by the reference glasses, i.e., the expressions are able to predict accurately the viscosity of a glass of interest as a function of temperature even if one or more of the $x_i$'s of the glass of interest is outside the range for that $x_i$ covered by the reference glasses.

Steps 4-10 relate to the determination of the fitting coefficients. In step 4, an initial set of fitting coefficients are chosen, and in step 5, those coefficients are used in the $\eta(T,x)$ equation to calculate viscosities for all the temperatures and compositions listed in the table of step 3. In step 6, an error is calculated by using, for example, the sum of squares of the deviations of log(viscosity) between calculated and measured values for all temperatures and all the compositions in the table of step 3. In step 7, this error is checked against previous errors. If this is the first time through step 7 or if the error has improved since the last time through step 7, the process branches to step 8.

In step 8, the fitting coefficients are adjusted in a direction that reduces the calculated error using one or more numerical computer algorithms known in the art, such as the Levenburg-Marquardt algorithm. Thereafter, steps 5-8 are repeated until the error is adequately small or cannot be further improved. The process then branches to step 9 where a check is made to see if the error has become "stuck" in a local minimum. For example, in this step, a new initial choice of fitting coefficients can be made and the process returned to steps 4-8 to see if a better solution is obtained. Finally, in step 10, the final choice of fitting coefficients are outputted, i.e., the fitting coefficients that give the least error in step 6 between measured viscosity values and calculated ones over all temperatures and compositions after all attempts at minimizing the error are completed. If desired, the $C_1$ and $C_2$ parameters of Eq. (1) can also be included in the error minimization process.

Figure 2:
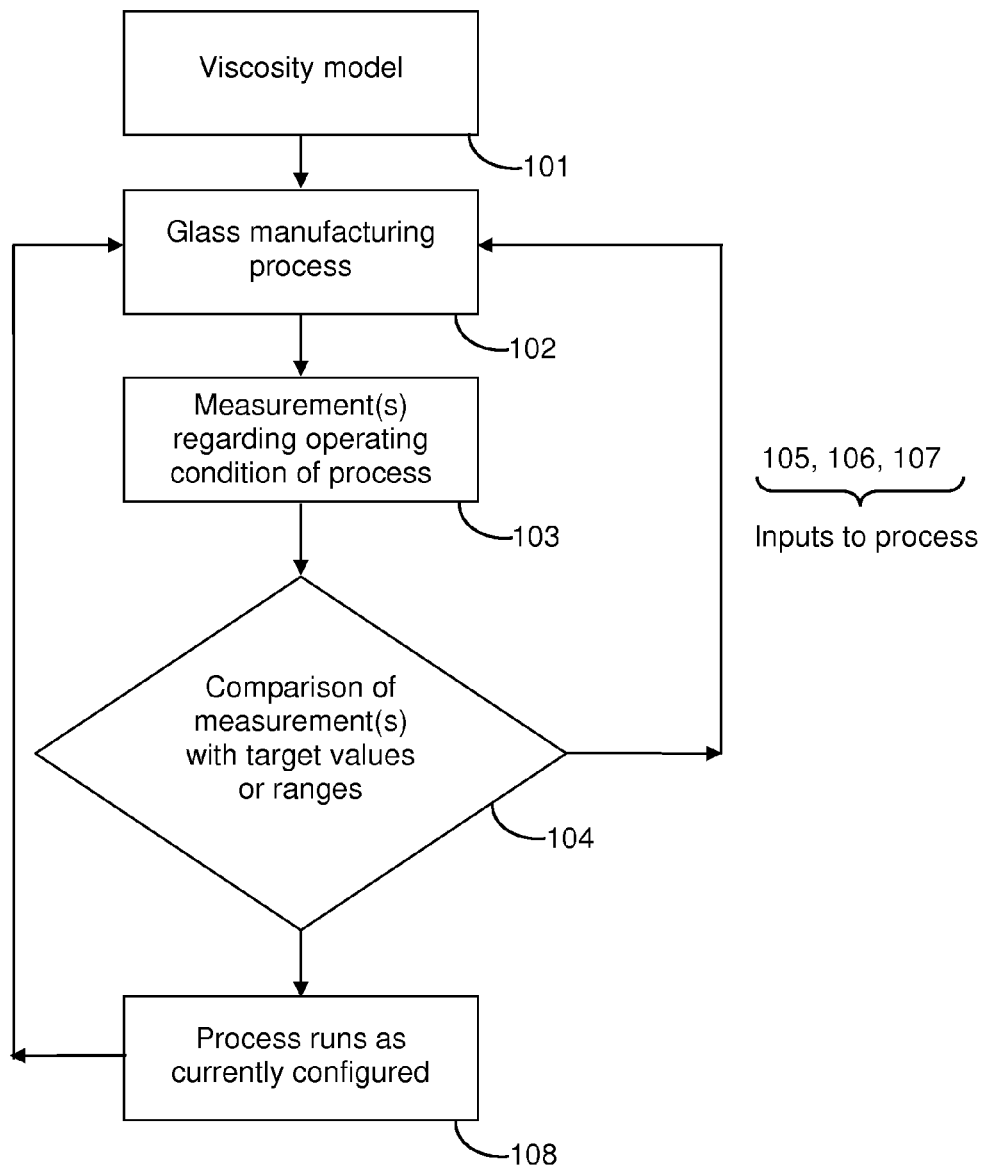
FIG. 2 is a flowchart showing a representative sequence of steps that can be used with a programmed computer to control a glass manufacturing process based on predictions of glass properties in accordance with embodiments of the present disclosure.

Once $C_1$, $C_2$, the $FC^1_i$'s, and the $FC^2_i$'s have been determined, Eq. (1) is complete and ready for use in a variety of applications. For example, as illustrated in the flowchart of FIG. 2, the $\eta(T,x)$ relationship can be used for process control.

In this figure, 101 represents a viscosity model according to the present disclosure which employs an $\eta(T,x)$ relationship having the form of Eq. (1) that has been programmed into a computer system so that calculations of viscosity for given temperatures and compositions can be made, while 102 represents a glass manufacturing process that, among other things, involves achieving a composition and obtaining given viscosities at given temperatures, where the composition and/or the temperatures can be varied by adjusting batching conditions and/or temperature (heating/cooling) controls. It should be noted that instead of containing $\eta(T,x)$, 101 can contain a lookup table stored in a computer memory of viscosity/temperature/composition information obtained using an expression for $\eta(T,x)$ having the form of Eq. (1). In this way, the need to evaluate the $\eta(T,x)$ relationship in real time can be avoided.

In 103, one or more measurements are made to reveal the operating condition of the 102 process. The measurements can, for example, be of temperature at one or more points in the process, and/or composition, and/or viscosity of the finished glass and/or the glass at one or more intermediate stages.

In 104, a comparison is made of the measurement or measurements of step 103 against target values or ranges for temperature, composition, and/or viscosity, as appropriate. If the comparison reveals that viscosity(s), temperature(s), and composition are within acceptable ranges, control transfers to 108 which permits the process to continue to run as currently configured. However, if the 104 comparison reveals a discrepancy between the measured value(s) and the target value(s) or range(s), an input (e.g., 105, 106) is generated and fed back to process 102.

Input 105 can be, for example, the response to a case where composition is found to have shifted slightly away from its target value, and can involve re-establishing a target viscosity at a given point in the process by shifting the temperature by an amount specified by the model of 101. Input 106 can again involve the case where composition is found to have shifted slightly away from its target value, but in this case the feedback response can be to re-establish the target viscosity at a given point in the process by altering the fraction of one or more selected viscosity-affecting components of the glass, with the choice of which component(s) to vary being governed by the viscosity model of 101, as well as other practical concerns such as other non-viscosity glass properties.

Input 107 represents a more general input to process 102 which may or may not be directly linked to measurement step 103 and comparison step 104. For example, 107 can represent a viscosity adjustment that is needed to improve the overall running of the process, e.g., an adjustment necessitated by a change in the source of a raw material. Such an adjustment can be achieved either by altering temperatures and/or by altering the fraction of viscosity-affecting components in a manner consistent with the viscosity model of 101.

It should, of course, be understood that the foregoing discussion of just three possible inputs into process 102 is for convenience of presentation only, and as will be evident to persons skilled in the art, a variety of other inputs are possible depending on the specifics of the particular glass manufacturing process to which the viscosity model disclosed herein is applied.

In addition to the process control application illustrated in FIG. 2, the $\eta(T,x)$ relationship can be used to discover new glass compositions meeting some desired set of viscosity criteria (e.g., melting point below a certain temperature and/or annealing point above a certain temperature). The steps in the discovery process can, for example, involve determining a desired range of viscosity isokom temperatures and then using Eq. (1) to generate quantitative viscosity-temperature-composition data to screen potential compositions for meeting the viscosity requirements. Results of the process can, for example, be reported as both the most optimum composition and the full range of compositions satisfying the desired viscosity properties.

More generally, viscosity predictions based on Eq. (1) can be used, for example, to guide experimental composition research, to pre-screen candidate glasses so as to reduce the number of compositions that need to be melted, and/or to reduce the number of low-temperature viscosity measurements that need to be performed, this last benefit being possible because accurate extrapolations to low temperatures are possible without systematic error. As discussed above, the form of Eq. (1) is physics-based, building on concepts from rigidity theory. As such, the model can extrapolate much more effectively compared to purely empirical models. In addition, because of their basis in physics, the values of the model parameters themselves offer physical insight into the role of each viscosity-affecting component in the network, which can provide the glass scientist with insights he/she would not otherwise have had.

Figure 3:
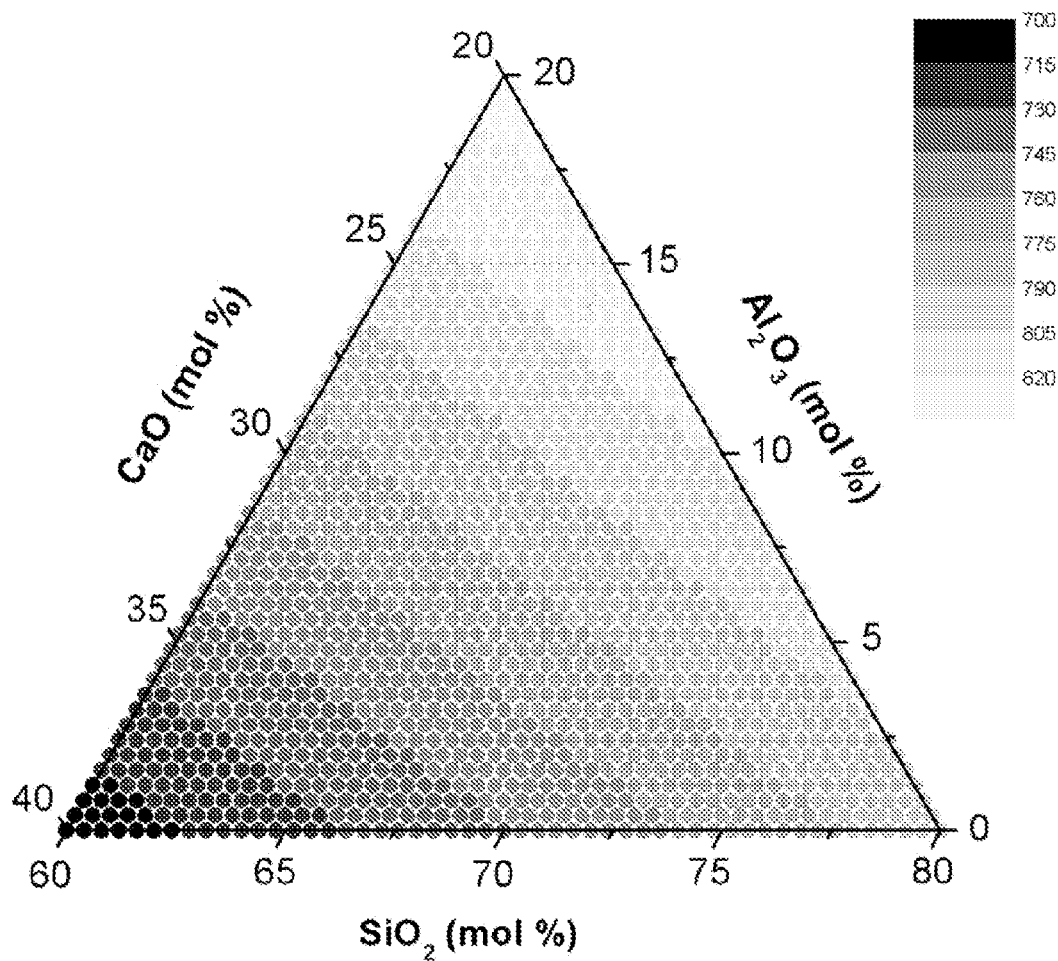
FIG. 3 is a ternary diagram for annealing temperature calculated using an embodiment of the present disclosure.

FIG. 3 illustrates one type of compositional research contemplated by the present disclosure. This ternary plot, calculated using the above viscosity model, shows the variation in annealing point in ° C. as a function of composition for a three-component hypothetical glass containing the oxides $SiO_2$, $Al_2O_3$, and $CaO$. The legend in this figure extends from 700° C. to 820° C. Plots of this kind can be used by glass scientists in guiding composition research to obtain optimized viscosity curves for a given application.

In addition to being highly effective in relating viscosity to temperature and composition, the form of Eq. (1) has been found to be highly effective in relating resistivity $\rho$ to these variables. In this case, Eq. (1) becomes:

$$\log_{10}\rho(T,x) = C^\rho_1 + C^\rho_2 \cdot (f_1(x,FC^\rho 1)/T) \cdot \exp([f_2(x,FC^\rho 2) - 1] \cdot [f_1(x,FC^\rho 1)/T - 1]) \quad \text{Eq. (7)}$$

where $C^\rho_1$, $C^\rho_2$, x, $FC^\rho 1$, and $FC^\rho 2$ are as defined above in the Summary.

As with viscosity, a particularly effective embodiment of Eq. (7) is one in which $f_1(x,FC^\rho 1)$ relates to glass transition temperature and $f_2(x,FC^\rho 2)$ relates to fragility. In this case, the resistivity version of Eq. (2) becomes:

$$\log_{10}\rho(T,x) = \log_{10}\rho_\infty + (12 - \log_{10}\eta_\infty)\frac{T_g(x)}{T}\exp\left[\left(\frac{m(x)}{12-\log_{10}\eta_\infty} - 1\right)\left(\frac{T_g(x)}{T} - 1\right)\right] \quad \text{Eq. (8)}$$

where $\rho_\infty$ is the extrapolated infinite temperature resistivity (e.g., $\rho_\infty = 10^{-4}$ Ω-m), and $\eta_\infty$, $T_g(x)$, and $m(x)$ are as defined above (see Eqs. (3)-(6)). Comparing Eq. (8) to Eq. (7), we see that in this embodiment:

$C^\rho_1 = \log_{10}\rho_\infty$, and $C^\rho_2 = 12 - \log_{10}\eta_\infty$.

Figure 4:
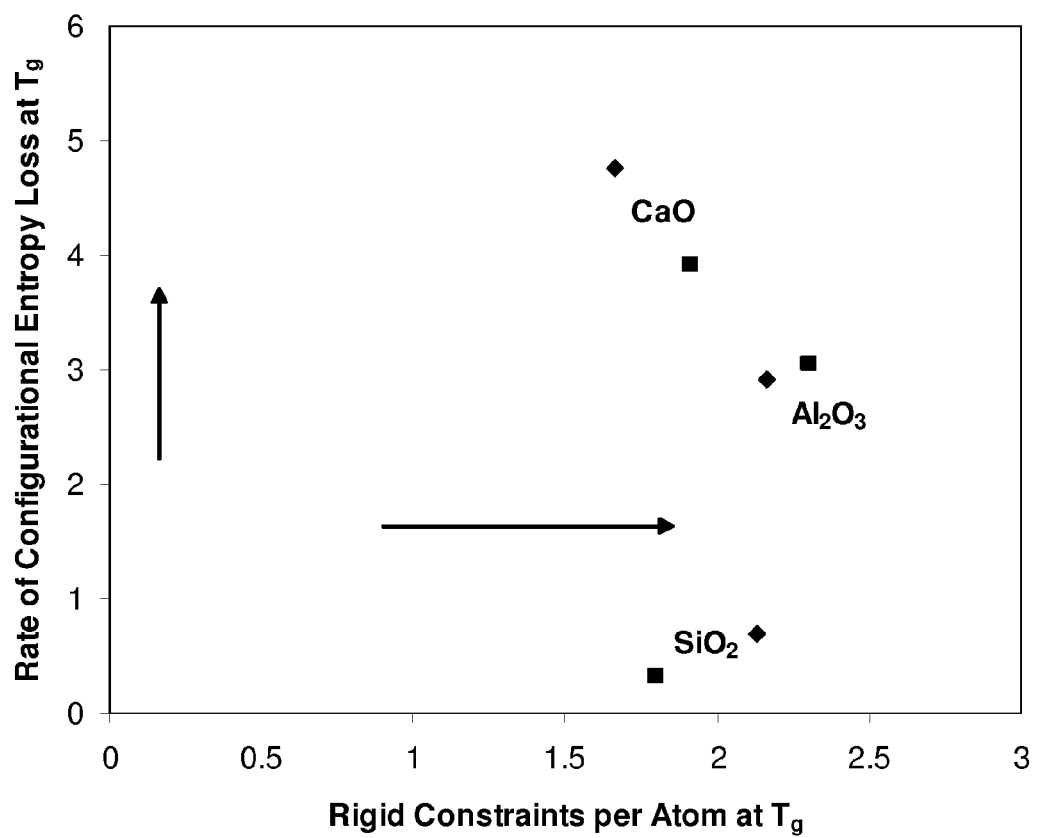
FIG. 4 is a plot illustrating fitting coefficients of embodiments of the present disclosure. For these embodiments, each viscosity-affecting or resistivity-affecting component has two parameters: the number of rigid constraints per atom and the rate of configurational entropy loss at the glass transition. A higher number of rigid constraints leads to a higher glass transition temperature, and a greater entropy loss leads to a larger value of fragility.

If desired, the $FC^1_i$'s and $FC^2_i$'s determined for the viscosity determination can be used as the $FC^{\rho 1}_i$'s and $FC^{\rho 2}_i$'s for the resistivity determination. However, in practice, it has been found that better resistivity predictions are achieved by performing a separate fit to resistivity data. FIG. 4 illustrates the types of shifts in $n_i$ values (horizontal axis) and $\Delta C_{p,i}/\Delta S_i$ values (vertical axis) that are observed. In this figure, the diamonds are the values obtained by fitting to viscosity data, while the squares are the values obtained by fitting to resistivity data. The horizontal arrow shows the direction of increasing $T_g$ while the vertical arrow shows the direction of increasing fragility.

As with viscosity, the fitting to obtain resistivity coefficients can be performed using techniques of the type illustrated in FIG. 1 and the resulting equation for $\rho(T,x)$ can be used to identify compositions having desired resistivity properties and/or to control a production process in a manner analogous to that illustrated in FIG. 2 for $\eta(T,x)$. In particular, the resistivity predictions are of particular value in controlling the melting stage of a glass manufacturing process. As will be evident from the present disclosure, the $\eta(T,x)$ and $\rho(T,x)$ predictions can be used in combination both with regard to identifying compositions having desirable properties and/or in controlling production processes. It should be noted that although a "production process" will normally be a commercial process, it can also be an experimental process, e.g., a laboratory scale process.

The mathematical procedures described above can be readily implemented using a variety of computer equipment and a variety of programming languages or mathematical computation packages such as MATHEMATICA (Wolfram Research, Champaign, Ill.), MATLAB (MathWorks of Natick, Mass.), or the like. Customized software can also be used. Output from the procedures can be in electronic and/or hard copy form, and can be displayed in a variety of formats, including in tabular and graphical form. For example, graphs of $\eta(T,x)$ and/or $\rho(T,x)$ can be prepared using commercially available data presentation software such as MICROSOFT's EXCEL program or similar programs. Software embodiments of the procedures described herein can be stored and/or distributed in a variety of forms, e.g., on a hard drive, diskette, CD, flash drive, etc. The software can operate on various computing platforms, including personal computers, workstations, mainframes, etc.

Without intending to limit it in any manner, the invention will be further illustrated by the following examples.

Example 1

This example illustrates the effectiveness of Eq. (1) in predicting viscosity as a function of temperature and/or composition.

Figure 5:
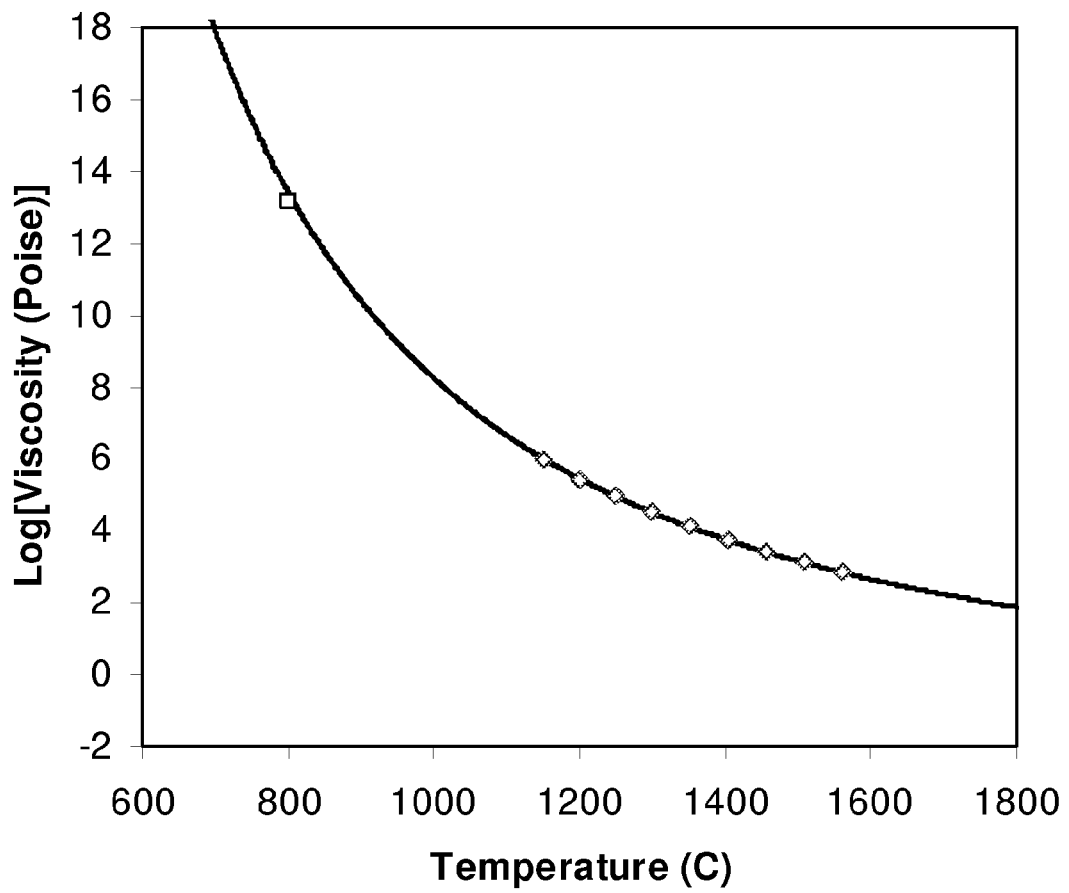
FIG. 5 shows a viscosity versus temperature curve obtained for a display-type glass using an equation for η(T,x) of the type set forth in Eq. (1). Experimental viscosity measurements performed on the glass are also plotted in this figure.

In particular, FIG. 5 illustrates the effectiveness of an equation of the form of Eq. (1) (specifically, Eq. (2)) in predicting viscosity as a function of temperature for a particular glass composition. In this case, the glass composition, which is suitable for display applications, contained six viscosity-affecting components, i.e., $SiO_2$, $Al_2O_3$, MgO, CaO, SrO, and BaO.

Fitting coefficients of the type shown in FIG. 4, i.e., FC1 and FC2 vectors, were obtained for the six viscosity-affecting components using a set of reference glasses and a fitting procedure of the type described above in connection with FIG. 1. In practice, it has been found that as the size of the family of reference glasses increases, the fitting coefficients settle down to essentially fixed values which show little or no variation as new experimental data is added to the reference collection. For this example, the family of reference glasses did not include the glass for which the predicted viscosity was calculated.

As shown in FIG. 5, the Eq. (1) model gave an excellent prediction of the viscosity curve over the entire range of temperatures, using only the composition of the glass as input. In this figure, the black curve is the extrapolation in composition space, the square data point represents the results of a fiber elongation measurement, and the diamond data points represent results of high temperature viscosity measurements.

Figure 6:
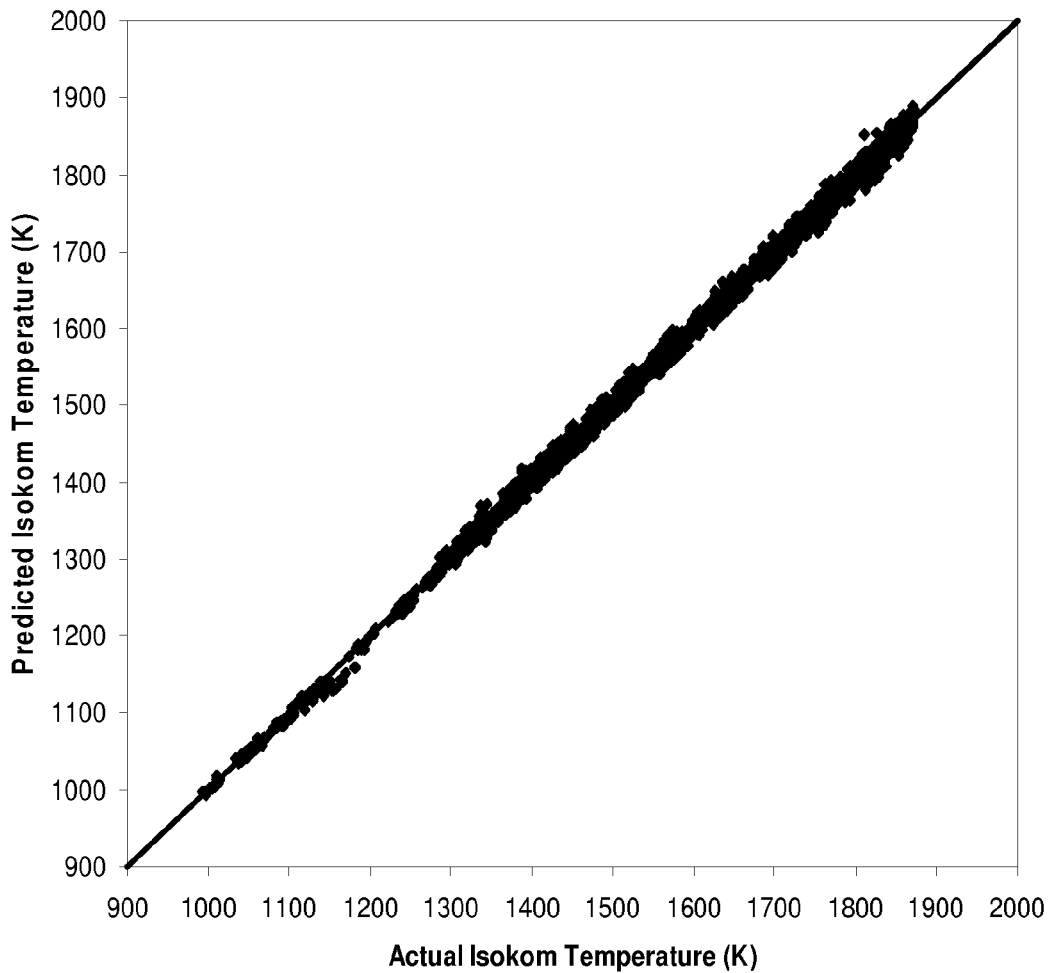
FIG. 6 is a plot comparing measured isokom temperatures with isokom temperatures predicted using an equation for η(T,x) of the type set forth in Eq. (1).

FIG. 6 shows the effectiveness of Eq. (1) over a wide range of temperatures and compositions. In this figure, the horizontal axis represents the results of over 7,000 viscosity measurements on over 750 different compositions, while the vertical axis represents the corresponding predicted temperature values obtained using an equation of the form of Eq. (1) (specifically, Eq. (2)) and an $n_i$ and a $\Delta C_{p,i}/\Delta S_i$ fitting coefficient for each of the viscosity-affecting components contained in the particular glass whose isokom temperature ($\rho=10$ Pa-s to $10^{11}$ Pa-s) was calculated. The RMS error in isokom temperature was only 6.55 K, a truly small value for this large a population of glasses.

Example 2

This example illustrates the effectiveness of Eq. (7) in predicting resistivity as a function of temperature and/or composition.

Figure 7:
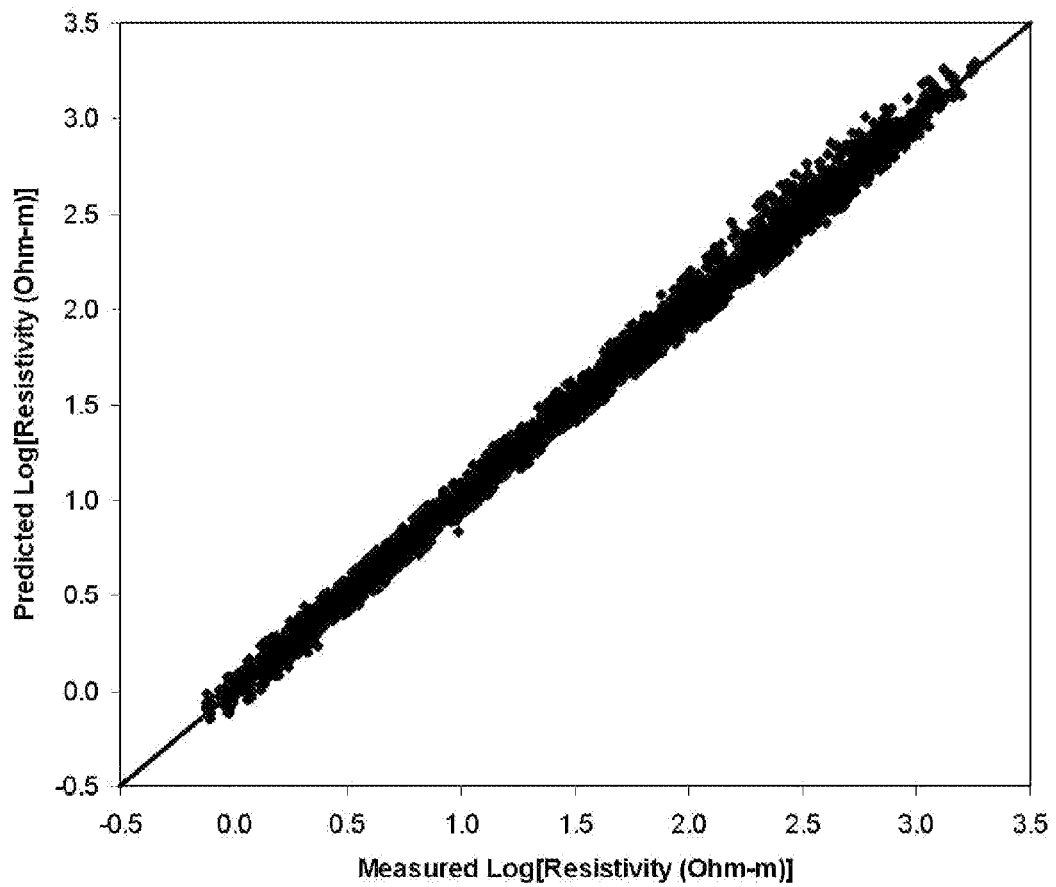
FIG. 7 is a plot comparing measured resistivity values with resistivity values predicted using an equation for ρ(T,x) of the type set forth in Eq. (7).

In particular, FIG. 7 compares predicted versus measured resistivity for over 7,500 resistivity measurements (units=ohm-meters) on over 800 compositions at a variety of temperatures. The predicted temperature values were obtained using an equation of the form of Eq. (7) (specifically, Eq. (8)) and an $n_i$ and a $\Delta C_{p,i}/\Delta S_i$ fitting coefficient for each of the resistivity-affecting components contained in the particular glass. The RMS error of the log values of FIG. 7 was 0.047. Importantly, both a fractional Stokes-Einstein model and a linear Stokes-Einstein model were found to give RMS errors of the log values more than 10 times higher for the same compositions and resistivity measurements, i.e., 0.137 and 0.134, respectively. The improved RMS error of the Eq. (7) model illustrates its effectiveness in predicting resistivity based on temperature and composition inputs.

From the foregoing, it can be seen that improved techniques for predicting the properties of glass materials, specifically, viscosity and resistivity, have been provided. A variety of modifications that do not depart from the scope and spirit of the invention will be evident to persons of ordinary skill in the art from this disclosure. The following claims are intended to cover the specific embodiments set forth herein as well as modifications, variations, and equivalents of those embodiments.

What is claimed is:

1. For a material that (a) is a glass or glass-forming liquid and (b) comprises N viscosity-affecting components, a method comprising (A) using a computer to evaluate an equation which relates equilibrium viscosity η and temperature T and has the following form:

$$\log_{10}\eta(T,x) = C_1 + C_2 \cdot (f_1(x,FC1)/T) \cdot \exp([f_2(x,FC2)-1] \cdot [f_1(x,FC1)/T-1])$$

where
(i) $C_1$ and $C_2$ are constants,
(ii) $x=\{x_1, x_2, \ldots x_i \ldots x_N\}$ are the concentrations of the N viscosity-affecting components,
(iii) $FC1=\{FC^1_1, FC^1_2 \ldots FC^1_i \ldots FC^1_N\}$ is a first set of empirical, temperature-independent fitting coefficients, one coefficient for each of the N viscosity-affecting components, and
(iv) $FC2=\{FC^2_1, FC^2_2 \ldots FC^2_i \ldots FC^2_N\}$ is a second set of empirical, temperature-independent fitting coefficients, one coefficient for each of the N viscosity-affecting components; and (B) using the results of step (A) to provide at least one of: (i) a predicted equilibrium viscosity η of the material at a temperature T, and (ii) a predicted temperature T at which the material has an equilibrium viscosity η.

2. The method of claim 1 wherein $f_1(x,FC1)$ relates to glass transition temperature $T_g$ and $f_2(x,FC2)$ relates to fragility m.

3. The method of claim 2 wherein $f_1(x,FC1)$ is given by:

$$f_1(x, FC1) = T_g(x) = \frac{K_R}{d - \sum_i x_i n_i \bigg/ \sum_i x_j N_j}$$

where the $n_i$'s are the $FC^1_i$'s, d is the dimensionality of space, the $N_j$'s are the numbers of atoms in the viscosity-affecting components, and $K_R$ is a scaling parameter for a selected reference material R, said scaling parameter being given by:

$$K_R = T_g(x_R)\left(d - \frac{\sum_i x_{R,i} n_i}{\sum_j x_{R,j} N_j}\right)$$

where $T_g(x_R)$ is a glass transition temperature for the reference material, said glass transition temperature being based on at least one viscosity measurement.

4. The method of claim 2 wherein $f_2(x,FC2)$ is given by:

$$f_2(x, FC2) = m(x)/m_0 = \left(1 + \sum_i x_i \frac{\Delta C_{p,i}}{\Delta S_i}\right)$$

where the $$\frac{\Delta C_{p,i}}{\Delta S_i}\text{'s}$$

are the $FC^2_i$'s and $m_0$ is $C_2$.

5. The method of claim 4 wherein $m_0$ satisfies the relationship:

$$16 > m_0 \geq 14.$$

6. The method of claim 4 wherein $m_0$ satisfies the relationship:

$$m_0 \approx 14.9.$$

7. The method of claim 2 wherein:

$$C_1 = \log_{10} \eta_\infty$$

wherein $\eta_\infty$ is an extrapolated infinite temperature viscosity.

8. The method of claim 7 wherein:

$$C_2 = 12 - C_1.$$

9. The method of claim 1 wherein an evaluation of an expression of the form $\log_{10}\eta(T,x) = C_1 + C_2 \cdot (f_1(x,FC1)/T) \cdot \exp([f_2(x,FC2)-1] \cdot [f_1(x,FC1)/T-1])$ gives an $\eta$ value that is greater than or equal to $10^8$ Pa-s.

10. The method of claim 1 wherein one or more of the viscosity-affecting components is a cluster of constituents of the material.

11. The method of claim 1 wherein one or more of the viscosity-affecting components is an oxide.

12. The method of claim 1 wherein one of the viscosity-affecting components is water.

13. The method of claim 1 wherein equilibrium viscosities are predicted at a plurality of temperatures and the results of the predictions are displayed as at least one of: (a) a viscosity versus temperature curve and (b) a temperature versus viscosity curve.

14. The method of claim 13 wherein equilibrium viscosities are predicted at a plurality of temperatures for a plurality of materials and the results of the predictions are displayed as a plurality of curves, one curve for each material.

15. The method of claim 1 further comprising using a predicted equilibrium viscosity in a glass manufacturing process to alter at least one operating temperature and/or the concentration of at least one viscosity-affecting component.

16. The method of claim 1 further comprising producing a lookup table of predicted equilibrium viscosities and using the lookup table in a glass manufacturing process to alter at least one operating temperature and/or the concentration of at least one viscosity-affecting component.

17. The method of claim 1 further comprising:
(a) performing steps (A) and (B) multiple times for one or more materials to produce at least one viscosity/temperature/composition relation; and
(b) using the at least one viscosity/temperature/composition relation in a feedback control system in a glass manufacturing process.

18. The method of claim 17 wherein the viscosity/temperature/composition relation is in the form of a lookup table.

19. The method of claim 1 wherein FC1 and FC2 are based on a set of reference materials and the material is not a reference material.

20. The method of claim 1 further comprising:
(a) using a computer to evaluate an equation which relates resistivity $\rho$ and temperature T and has the following form:

$$\log_{10}\rho(T,x) = C^\rho_1 + C^\rho_2 \cdot (f_1(x,FC^\rho 1)/T) \cdot \exp([f_2(x,FC^\rho 2)-1] \cdot [f_1(x,FC^\rho 1)/T-1])$$

where
(i) $C^\rho_1$ and $C^\rho_2$ are constants,
(ii) $x = \{x_1, x_2, \ldots x_i \ldots x_{N'}\}$ are the concentrations of N' resistivity-affecting components of the material,
(iii) $FC^\rho 1 = \{FC^\rho_1, FC^\rho_2 \ldots FC^\rho_i \ldots FC^\rho_{N'}\}$ is a first set of empirical, temperature-independent fitting coefficients, one coefficient for each of the N' resistivity-affecting components, and
(iv) $FC^\rho 2 = \{FC^\rho_1, FC^\rho_2 \ldots FC^\rho_i \ldots FC^\rho_{N'}\}$ is a second set of empirical, temperature-independent fitting coefficients, one coefficient for each of the N' resistivity-affecting components, and
(b) using the results of step (a) to provide at least one of: (i) a predicted electrical resistivity $\rho$ of the material at a temperature T, and (ii) a predicted temperature T at which the material has an electrical resistivity $\rho$.

21. The method of claim 20 wherein N=N'.

22. Apparatus comprising a computer which has been programmed to perform steps (A) and (B) of claim 1.

23. An article of manufacture comprising a non-transitory computer readable storage medium having computer readable code embodied therein for performing steps (A) and (B) of claim 1.

24. A method for identifying at least one material expected to have at least one desired $\eta,T$ pair, where $\eta$ is equilibrium viscosity and T is temperature, said method comprising:
(A) selecting at least one candidate material comprising N viscosity-affecting components having selected concentrations, where N may be different for different candidate materials;
(B) using a computer to obtain at least one $\eta,T$ pair for the at least one candidate material of step (A) by evaluating an expression of the form $$\log_{10}\eta(T,x) = C_1 + C_2 \cdot (f_1(x,FC1)/T) \cdot \exp([f_2(x,FC2)-1] \cdot [f_1(x,FC1)/T-1])$$

where
$C_1$ and $C_2$ are constants,
(ii) $x = \{x_1, x_2, \ldots x_i \ldots x_N\}$ are the concentrations of the N viscosity-affecting components,
(iii) $FC1 = \{FC^1_1, FC^1_2 \ldots FC^1_i \ldots FC^1_N\}$ is a first set of empirical, temperature-independent fitting coefficients, one coefficient for each of the N viscosity-affecting components, and
(iv) $FC2 = \{FC^2_1, FC^2_2 \ldots FC^2_i \ldots FC^2_N\}$ is a second set of empirical, temperature-independent fitting coefficients, one coefficient for each of the N viscosity-affecting components;
(C) comparing the at least one $\eta,T$ pair resulting from step (B) with the at least one desired $\eta,T$ pair; and
(D) repeating steps (A) to (C) as necessary until at least one candidate material is selected in step (A) which gives at least one $\eta,T$ pair in step (B) which satisfies at least one selected criterion relative to the at least one desired $\eta,T$ pair, said at least one candidate material being the at least one material expected to have the at least one desired $\eta,T$ pair.

25. The method of claim 24 wherein the at least one selected criterion comprises the difference in $\eta$ being less than a first selected value when the difference in T is less than a second selected value.

26. The method of claim 24 wherein FC1 and FC2 are based on a set of reference materials and at least one of the $x_i$ of at least one candidate material is outside the range of $x_i$'s of the reference set of materials.

27. The method of claim 24 wherein evaluations of the expression extend over a range of at least 4 orders of magnitude.

28. A method of determining a relationship between temperature T and viscosity $\eta$ for a material that (i) is a glass or glass-forming liquid and (ii) comprises N viscosity-affecting components, said method comprising:
  (a) measuring the viscosity of a plurality of reference materials at a plurality of temperatures;
  (b) using a programmed computer, fitting a function of the form $$\log_{10}\eta(T,x)=C_1+C_2\cdot(f_1(x,FC1)/T)\cdot\exp([f_2(x,FC2)-1]\cdot[f_1(x,FC1)/T-1])$$

to the measured viscosities of step (a) to determine values for FC1 and FC2, where in said function:
    (i) $C_1$ and $C_2$ are constants,
    (ii) $x=\{x_1, x_2, \ldots x_i \ldots x_N\}$ are the concentrations of the N viscosity-affecting components,
    (iii) $FC1=\{FC^1_1, FC^1_2 \ldots FC^1_i \ldots FC^1_N\}$ is a first set of temperature-independent coefficients, one coefficient for each of the N viscosity-affecting components, and
    (iv) $FC2=\{FC^2_1, FC^2_2 \ldots FC^2_i \ldots FC^2_N\}$ is a second set of temperature-independent coefficients, one coefficient for each of the N viscosity-affecting components,
  said function and the values for FC1 and FC2 determined in step (b) constituting the relationship between viscosity and temperature for the material; and
  (c) using the results of step (b) to provide at least one of: (i) a predicted equilibrium viscosity $\eta$ of the material at a temperature T, and (ii) a predicted temperature T at which the material has an equilibrium viscosity $\eta$.

29. For a material that (a) is a glass or glass-forming liquid and (b) comprises N' resistivity-affecting components, a method comprising
  (A) using a computer to evaluate an equation which relates resistivity $\rho$ and temperature T and has the following form:

$$\log_{10}\rho(T,x)=C^p_1+C^p_2\cdot(f_1(x,FC^p1)/T)\cdot\exp([f_2(x,FC^p2)-1]\cdot[f_1(x,FC^p1)/T-1])$$

where
    (i) $C^p_1$ and $C^p_2$ are constants,
    (ii) $x=\{x_1, x_2, \ldots x_i \ldots x_{N'}\}$ are the concentrations of the N' resistivity-affecting components,
    (iii) $FC^p1=\{FC^p_1, FC^p_2 \ldots FC^p_i \ldots FC^p_{N'}\}$ is a first set of empirical, temperature-independent fitting coefficients, one coefficient for each of the N' resistivity-affecting components, and
    (iv) $FC^p2=\{FC^p_1, FC^p_2 \ldots FC^p_i \ldots FC^p_{N'}\}$ is a second set of empirical, temperature-independent fitting coefficients, one coefficient for each of the N' resistivity-affecting components, and
  (B) using the results of step (A) to provide at least one of: (i) a predicted resistivity $\rho$ of the material at a temperature T, and (ii) a predicted temperature T at which the material has a resistivity $\rho$.

30. A method for identifying at least one material expected to have at least one desired $\rho$,T pair, where $\rho$ is resistivity and T is temperature, said method comprising:
  (A) selecting at least one candidate material comprising N' resistivity-affecting components having selected concentrations, where N' may be different for different candidate materials;
  (B) using a computer to obtain at least one $\rho$,T pair for the at least one candidate material of step (A) by evaluating an expression of the form $$\log_{10}\rho(T,x)=C^p_1+C^p_2\cdot(f_1(x,FC^p1)/T)\cdot\exp([f_2(x,FC^p2)-1]\cdot[f_1(x,FC^p1)/T-1])$$

where
    (i) $C^p_1$ and $C^p_2$ are constants,
    (ii) $x=\{x_1, x_2, \ldots x_i \ldots x_{N'}\}$ are the concentrations of the N' resistivity-affecting components,
    (iii) $FC^p1=\{FC^p_1, FC^p_2 \ldots FC^p_i \ldots FC^p_{N'}\}$ is a first set of empirical, temperature-independent fitting coefficients, one coefficient for each of the N' resistivity-affecting components, and
    (iv) $FC^p2=\{FC^p_1, FC^p_2 \ldots FC^p_i \ldots FC^p_{N'}\}$ is a second set of empirical, temperature-independent fitting coefficients, one coefficient for each of the N' resistivity-affecting components,
  (C) comparing the at least one $\rho$,T pair resulting from step (B) with the at least one desired $\rho$,T pair; and
  (D) repeating steps (A) to (C) as necessary until at least one candidate material is selected in step (A) which gives at least one $\rho$,T pair in step (B) which satisfies at least one selected criterion relative to the at least one desired $\rho$,T pair, said at least one candidate material being the at least one material expected to have the at least one desired $\rho$,T pair.

31. A method of determining a relationship between temperature T and resistivity $\rho$ for a material that (i) is a glass or glass-forming liquid and (ii) comprises N' resistivity-affecting components, said method comprising:
  (a) measuring the resistivity of a plurality of reference materials at a plurality of temperatures;
  (b) using a programmed computer, fitting a function of the form $$\log_{10}\rho(T,x)=C^p_1+C^p_2\cdot(f_1(x,FC^p1)/T)\cdot\exp([f_2(x,FC^p2)-1]\cdot[f_1(x,FC^p1)/T-1])$$

to the measured resistivities of step (a) to determine values for $FC^p1$ and $FC^p2$, where in said function:
    (i) $C^p_1$ and $C^p_2$ are constants,
    (ii) $x=\{x_1, x_2, \ldots x_i \ldots x_{N'}\}$ are the concentrations of the N' resistivity-affecting components,
    (iii) $FC^p1=\{FC^p_1, FC^p_2 \ldots FC^p_i \ldots FC^p_{N'}\}$ is a first set of temperature-independent coefficients, one coefficient for each of the N' resistivity-affecting components, and
    (iv) $FC^p2=\{FC^p_1, FC^p_2 \ldots FC^p_i \ldots FC^p_{N'}\}$ is a second set of temperature-independent coefficients, one coefficient for each of the N' resistivity-affecting components,
  said function and the values for $FC^p1$ and $FC^p2$ determined in step (b) constituting the relationship between resistivity and temperature for the material; and
  (c) using the results of step (b) to provide at least one of: (i) a predicted equilibrium resistivity $\rho$ of the material at a temperature T, and (ii) a predicted temperature T at which the material has an equilibrium resistivity $\rho$.

\* \* \* \* \*